United States Patent [19]

Ebata et al.

[11] Patent Number: 5,264,561
[45] Date of Patent: Nov. 23, 1993

[54] METHOD OF MANUFACTURING 2',3'-DIDEOXY-2',3'-DIDEHYDRONUCLEOSIDES

[75] Inventors: Takashi Ebata; Hajime Matsushita, both of Yokohama; Nobuhiro Mizutani, Tokyo; Junji Ohki, Tokyo; Junko Tanaka, Tokyo; Hiromi Kaibara, Tokyo; Kazuo Itoh, Tokyo, all of Japan

[73] Assignees: Japan Tobacco Inc.; Yuki Gosei Kogyo Co, Ltd., both of Tokyo, Japan

[21] Appl. No.: 854,843

[22] Filed: Mar. 20, 1992

[30] Foreign Application Priority Data

Mar. 22, 1991 [JP] Japan .................. 3-058872

[51] Int. Cl.$^5$ ............................................. C07H 19/00
[52] U.S. Cl. .................... 536/27.14; 536/28.2
[58] Field of Search ............ 536/23, 120, 27.14, 536/28.2

[56] References Cited

FOREIGN PATENT DOCUMENTS

| | | |
|---|---|---|
| 52-27782 | 3/1977 | Japan . |
| 52-93779 | 8/1977 | Japan . |
| 53-147089 | 12/1978 | Japan . |
| 53-108982 | 9/1979 | Japan . |
| 63-83048 | 4/1988 | Japan . |
| 25496 | 11/1988 | Japan . |
| 63264596 | 2/1989 | Japan . |

OTHER PUBLICATIONS

Jain et al. (1974) *J. Org. Chem.*, 39(1):30–38.
Shiragami et al. (1988) *J. Org. Chem.*, 53:5170–5173.
Chu et al. (1989) *J. Org. Chem.*, 54:2217–25.
Shibagaki et al. (1990) *Chemistry Letters (The Chemical Society of Japan)* pp. 307–310.
Barton et al. (1991) *Tetrahedron Letters*, 32(23):2569–72.
McCarthy et al. (1966) Jour. Am. Chem. Soc., 88(7) 1550–53.
Horwitz et al. (1967) Notes, vol. 32, pp. 817–818.
Griffin et al. (1967) Tetrahedron (23):2301–13.

*Primary Examiner*—Johnnie R. Brown
*Assistant Examiner*—J. Oliver Wilson

[57] ABSTRACT

The instant invention is drawn to a method for manufacturing 2',3'-dideoxy-2',3'-didehydronucleoside compounds by reacting a ribonucleoside derivative wherein the hydroxyl in the 5'-position of the furanose ring of said ribonucleoside is protected by a silyl protective group, with an acid anhydride such as acetic anhydride in the presence of a catalyst such as hydrous zirconium oxide, and then subjecting the reaction product to decarboxylation. The decarboxylation can be effected by heating the reaction product. This method can be performed in a single step, and requires no reagents which are expensive or chemicals which should be handled with care. Hence, it serves to manufacture 2',3'-dideoxy-2',3'-didehydronucleosides easily at low cost.

15 Claims, No Drawings

METHOD OF MANUFACTURING 2',3'-DIDEOXY-2',3'-DIDEHYDRONUCLEOSIDES

BACKGROUND OF THE INVENTION

1. Field of the Invention

The present invention relates to a method of manufacturing 2',3'-dideoxy-2',3'-didehydronucleosides.

2. Description of the Related Art

2',3'-dideoxy-2',3'-didehydronuclesides are resistant to viruses and cancer. Further, they are known as anti-HIV agents and are, therefore, useful as raw materials for the production of medicines. They are represented by the following general formula (I):

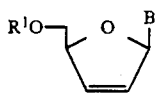
(I)

where $R^1$ is a silyl protective group, and B is a purine base or a pyrimidine base.

Various methods of manufacturing 2',3'-dideoxy2',3'-didehydronucleosides are known. Methods wherein a ribonucleoside is used are described in The Journal of the Organic Chemistry 39, 30 (1974), The Journal of the Organic Chemistry 53, 5170 (1988), and The Journal of the Organic Chemistry 54, 2217 (1989). Methods wherein a 2'-deoxynucleoside is used are disclosed in The Journal of the American Chemical Society 88, 1549 (1966) and The Journal of the Organic Chemistry 32, 817 (1967).

Most of the known methods described above comprise many steps, and require the use of costly reagents as raw materials. They achieve but a low yield and are not economical. Thus, they are unfit for industrial use.

SUMMARY OF THE INVENTION

It is therefore the object of the present invention to provide a method of manufacturing 2',3'-dideoxy-2',3'-didehydronucleosides with ease and at low cost.

According to this invention, there is provided a method of manufacturing 2',3'-dideoxy-2',3'-didehydronucleosides, comprising the steps of:

reacting a ribonucleoside derivative with an acid anhydride in the presence of a catalyst, said ribonucleoside derivative being of the following general formula (II):

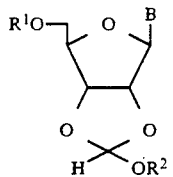
(II)

where $R^1$ is a silyl protective group, $R^2$ is an alkyl or phenyl group which may have substituents in some cases, and B is a purine or pyrimidine base, and causing the resultant material to decarboxylate.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The present inventors, have invented a method of manufacturing 2',3'-dideoxy-2',3'-didehydronucleosides with ease and at low cost, in which a specific ribonucleoside derivative is made to react with an acid anhydride in the presence of a catalyst, and the resultant material is decarboxylated under neutral or basic conditions, as is claimed in Japanese Patent Application No. 2-338649. This latter method, however, must be conducted in two steps since the decarboxylation should be effected under neutral or basic conditions while the reaction system is acidified after the reaction between a ribonucleoside derivative and an acid anhydride. It was found to be possible to manufacture 2',3'-dideoxy-2',3'-didehydronucleosides in a single step by effecting the decarboxylation not under basic conditions, provided that the 5-position hydroxyl group of the furanose ring of the ribonucleoside derivative is protected by a silyl protective group. The present invention is based on this finding. In the present specification, the term "two steps" means that the manufacturing process includes the step of neutralizing or alkalizing the reaction system after the reaction between a ribonucleoside derivative and an acid anhydride. In contrast, the term "single step" means that the series of reactions in the manufacturing process is conducted continuously.

The starting material used in the method of the invention, i.e., the compound of formula (II), can be converted from a ribonucleoside of the following formula (IV), either natural or manufactured, by the method described in, for example, Tetrahedron, 23, 2301 (1967):

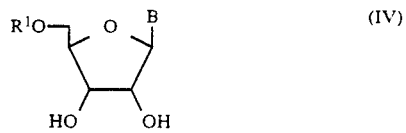
(IV)

where $R^1$ is a silyl protective group, and B is a purine base or a pyrimidine base.

The group $R^1$ included in the ribonucleoside derivative of formula (II) is a silyl protective group. Examples of this protective group are triorganosilyl groups such as trimethylsilyl, triethylsilyl, t-butyl dimethyl silyl, and t-butyl diphenyl silyl. Nonetheless, the protective group is not limited to these. An additional phenyl group, if contained in the protective group, can be a substituted phenyl group which has a substituent, for example, such as a halogen atom, an alkyl group, a nitro group, or an alkoxy group.

The group $R^2$ included in the ribonucleoside derivative of formula (II) is an alkyl group such as methyl or ethyl, or a phenyl group which may have a substituent.

The group B included in the ribonucleoside derivative of formula (II) is a series of bases consisting of pyrimidine bases or purine bases. The pyrimidine base includes uracil, cytosine, thymine, 5-fluorouracil, 5-chlorouracil, 5-bromouracil, 5-iodouracil, 5-ethyluracil, 5-trifluoromethyl uracil, 5-carboxyl uracil, and the like. The purine base includes adenine, guanine, hypoxanthine, xanthine, 2-chloropurine, 6-chloropurine, 2,6-dichloropurine, 2-amino-6-chloropurine, 2,6- diaminopurine, 6-mercaptopurine, 6-methyl thiopurine, 2-aminopurine, and the like. Nonetheless, the pyrimidine base and the purine base are not limited to these examples.

As has been described, in the method according to the present invention, a ribonucleoside derivative of formula (II) is made to react with an acid anhydride in the presence of a catalyst, and the resultant material is decarboxylated by means of, for example, heating. The reaction and the decarboxylation can be performed in one and the same step.

The reaction is carried out at 0° to 200° C. for 30 minutes to 24 hours.

Examples of the acid anhydride to react with the ribonucleoside derivative (II) are: acetic anhydride, chloroacetic anhydride, dichloroacetic anhydride, trichloroacetic anhydride, trifluoroacetic anhydride, benzoic, anhydride, propionic anhydride, and the like. These anhydrides can be used singly or, if desired, together with another solvent such as xylene, N,N-dimethyl formamide, butyl acetate or nitrobenzene.

The catalyst used in the method of the present invention is, for example, a solid acid such as hydrous zirconium oxide, hydrous titanium oxide, hydrous aluminum oxide, hydrous tin oxide, titanium oxide, zirconium oxide, silica gel, alumina or zeolite; an organic acid such as acetic acid, propionic acid, or p-toluenesulfonic acid; a mineral acid such as hydrochloric acid, sulfuric acid or phosphoric acid; or an acidic ion exchange resin. It is particularly desirable to use hydrous zirconium oxide.

The reaction proceeds even if no catalyst is used. If no catalyst is used, however, the rate of forming the 2'3'-dideoxy-2',3'-didehydronucleoside (I) is very low, and the acid present in the reaction system cleaves the glycoside bond of the compound (I) thus formed, ultimately decomposing the compound (I). It is, therefore, desirable that the reaction for forming the compound (I) be completed in a short time. The longer the reaction time, the lower the yield.

The product of the reaction is purified by ordinary methods such as extraction or recrystallization and, in some cases, is deprotected as desired, thereby obtaining a 2'3'-dideoxy-2',3'-didehydronucleoside represented by formula (I).

The present invention will now be described, with reference to some examples.

EXAMPLE 1

5'-(O-t-butyl diphenyl silyl)-2',3'-dideoxy-2',3'-didehydroinosine was manufactured in the following way.

First, 1.5 ml (14.7 mmol) of acetic anhydride was added to 0.45 mmol of 5'-(O-t-butyl diphenylsilyl)-2',3'-O-methoxy methylidene, and then this was heated at 100° C. for 1 hour. Next, 100 mg of hydrous zirconium oxide (HZO), used as catalyst, was added to the reaction mixture. This was heated at 130° C. for 0.75 hours, whereby 5'-(O-t-butyl diphenylsilyl)-2',3'-dideoxy-2',3'-didehydroinosine was obtained in a yield of 5%. The product exhibited the following physical properties:

$^1$H-NMR (200 MHz): δ (ppm) CDCl$_3$; 8.11 (s, 1H, 2-H), 7.84 (s, 1H, 8-H), 7.62–7.27 (m, 10H, Ph$_2$Si), 7.01–6.98 (m, 1H, 1'-H), 6.44 (dt, 1H, J=1.7, and 6.0 Hz, 3'-H), 6.02 (dt, 1H, J=1.8, and 5.9 Hz, 2'-H), 5.02–4.98 (m, 1H, 4'-H), 3.80–3.74 (m, 2H, 5'-H), 1.03 (s, 9H, Me$_3$CSi).

Color and shape: White, needle-like crystals.
Melting point: 176° C. (decomposed).

COMPARATIVE EXAMPLE 1

5'-(O-t-butyl diphenylsilyl)-2',3'-dideoxy-2',3'-didehydroinosine was manufactured in the same way as in Example 1, except that no catalyst was used and the reaction time was 6.0 hours. The yield of the product was 0.5%.

EXAMPLES 2 TO 4

Three samples of 5'-(O-t-butyl diphenylsilyl)-2',2'-dideoxy-2',3'-didehydroinosine, hereinafter referred to as Examples 2, 3 and 4, respectively, were manufactured in the same way as in Example 1, except in the following three respects, in order to determine how the catalyst used would influence the yield of the product. First, hydrous titanium oxide (HTO), alumina and acetic acid, not hydrous zirconium oxide, were used as catalysts in Examples 2, 3 and 4, respectively. Second, in Examples 3 and 4, the mixture containing the catalyst was heated for 5.0 hours, not for 0.75 hours. Third, alumina was used in Example 3 in an amount (300 mg) three times greater than usual, and acetic acid was used in an amount of 1.35 mmol (81 mg) in Example 4. The yields of Examples 2, 3 and 4 were as is shown in Table 1, along with that of Example 1:

TABLE 1

| Example | Catalyst | (mg) | Reaction Time (hr.) | Yield (%) |
| --- | --- | --- | --- | --- |
| 1 | HZO | 100 | 0.75 | 5 |
| 2 | HTO | 100 | 0.75 | 4 |
| 3 | Al$_2$O$_3$ | 300 | 5.0 | 3 |
| 4 | Acetic acid | 81 | 5.0 | 6 |

EXAMPLES 5 TO 7

Three samples of 5'-(O-t-butyl diphenylsilyl)-2',3'-dideoxy-2',3'-didehydroinosine, hereinafter referred to as Examples 5, 6 and 7, respectively, were manufactured in the same way as in Example 1, except in the following two respects, in order to determine how the concentration of the solvent used would influence the yield of the product. First, three mixtures of xylene and acetic anhydride (diluted acetic anhydride), the amount of each of which is shown in Table 2, were used as solvents in Examples 5, 6, and 7, respectively. Second, the reaction after the addition of the catalyst was carried out for 1.0 hours, not for 0.75 hours. The yields of Examples 5, 6 and 7 were as is shown in Table 2.

TABLE 2

| Example | Xylene (ml) | Acetic Anhydride (mmol) | Yield (%) |
| --- | --- | --- | --- |
| 5 | 1.4 | 1.125 | 14 |
| 6 | 1.3 | 2.25 | 14 |
| 7 | 1.1 | 4.5 | 6 |

COMPARATIVE EXAMPLE 2

5'-(O-t-butyl diphenylsilyl)-2',3'-dideoxy-2',3'-didehydroinosine was manufactured in the same way as in Example 1, except in three respects. First, no catalyst was used. Second, use was made of a mixture of 1.3 ml of xylene and 2.25 mmol of acetic anhydride as a solvent. Third, the reaction time was 5.0 hours. The yield of this product was 0.9%.

EXAMPLE 8

5'-(O-t-butyl diphenylsilyl)-2',3'-dideoxy-2',3'-didehydroinosine was manufactured in the same way as in Example 1, except in three respects. First, a mixture of 1.3 ml of xylene and 2.25 mmol (0.23 g) of acetic anhydride was used in place of acetic anhydride. Second, 100 mg of SK1B (a strongly acidic ion exchange resin which is commercially available) was used in place of HZO. Third, the reaction after the addition of the catalyst was performed for 3.0 hours, not for 0.75 hours. The yield of this product was 17%.

EXAMPLES 9 TO 14

Six samples of 5'-(O-t-butyl diphenylsilyl)-2',3'-dideoxy-2',3'-didehydroinosine, which will be referred to as Examples 9, 10, 11, 12, 13 and 14, were manufactured in the same way as in Example 1, except in three respects, in order to determine how the reaction temperature and the reaction time would influence the yield of the product. First, a mixture of 1.3 ml of xylene and 2.25 mmol of acetic anhydride was used as a solvent in place of acetic anhydride. Second, the reaction was performed at the temperatures specified in Table 3. Third, after the addition of the catalyst, the reaction was carried for the various times set forth in Table 3. The yields of Examples 9 to 14 were specified in Table 3.

TABLE 3

| Example | Reaction Time (hour) | Temperature (°C.) | Yield (%) |
|---|---|---|---|
| 9 | 0.5 | 130 | 9 |
| 10 | 1.5 | 100 | 14 |
| 11 | 1.0 | 110 | 11 |
| 12 | 1.0 | 120 | 23 |
| 13 | 0.5 | 140 | 7 |
| 14 | 0.5 | 130 | 13 |

EXAMPLES 15 AND 16

Two samples of 5'-(O-t-butyl diphenylsilyl)2',3'-dideoxy-2',3'-didehydroinosine, which will be referred to as Examples 15 and 16, were manufactured in the same way as Example 1, except in five respects, in order to determine how the yield of the product would change if the reaction was carried out at a relatively low temperature. First, the reaction was performed at 100° C. Second, the amount of the starting material (i.e., 5'-(O-t-butyl diphenylsilyl)-2',3'-O-methoxy methylidene) used was 0.9 mmol. Third, a mixture of 2.6 ml of xylene and 2.25 mmol of acetic anhydride was used as a solvent in place of acetic anhydride. Fourth, the amount of HZO was changed as set forth in Table 4. Fifth, the reaction after the addition of the catalyst was carried out for different periods set forth in Table 4. The yields of Examples 15 and 16 were as is specified in Table 4.

TABLE 4

| Example | Catalyst (mg) | Reaction Time (hour) | Yield (%) |
|---|---|---|---|
| 15 | HZO 200 | 5.0 | 15 |
|  |  | 21.0 | 54 |
| 16 | HZO 600 | 5.0 | 28 |

COMPARATIVE EXAMPLE 3 with acetyl group used as protective group

5'-(O-acetyl)-2',3'-O-methoxy methylideneinosine was used as starting material in order to manufacture 5'-(O-acetyl)-2',3'-dideoxy-2',3'-didehydroinosine.

First, 3.0 ml (29.4 mmol) of acetic anhydride was added to 0.9 mmol of the starting material, and then this was heated at 100° C. for 1 hour. Next, 200 mg of hydrous zirconium oxide (HZO), used as catalyst, was added to the reaction mixture. This was heated at 100° C. for 4 hours. The yield of 5'-(O-acetyl)-2',3'-dideoxy-2',3'-didehydroinosine was 0%.

COMPARATIVE EXAMPLE 4 with dimethoxymethyl group used as protective group

5'-(O-dimethoxymethyl)-2',3'-O-methoxy methylideneinosine was used as starting material in order to manufacture 5'-(O-dimethoxymethyl)-2',3'-dideoxy-2',3'-didehydroinosine.

First, 3.0 ml (29.4 mmol) of acetic anhydride was added to 0.9 mmol of the starting material, and then this was heated at 100° C. for 1 hour. Next, 200 mg of hydrous zirconium oxide (HZO), used as catalyst, was added to the reaction mixture. This was heated at 130° C. for 1.5 hours. The yield of 5'-(O-dimethoxymethyl)2',3'-dideoxy-2',3'-didehydroinosine was 0%.

COMPARATIVE EXAMPLE 5 with p-chlorobenzoyl group used as protective group

5'-(O-p-chlorobenzoyl)-2',3'-O-methoxy methylideneinosine was used as starting material in order to manufacture 5'-(O-p-chlorobenzoyl)-2',3'-dideoxy-2',3'-didehydroinosine.

First, 1.5 ml (14.7 mmol) of acetic anhydride was added to 0.45 mmol of the starting material, and then this was heated at 100° C. for 1 hour. Next, 100 mg of hydrous titanium oxide (HTO), used as catalyst, was added to the reaction mixture. This was heated at 130° C. for 1 hours. The yield of 5'-(O-p-chloro-benzoyl)-2',3'-dideoxy-2',3'-didehydroinosine was 0%.

As can be understood from the above, the method of the present invention serves to manufacture 2',3'-dideoxy-2',3'-didehydronucleosides easily at low cost, without using reagents which are expensive or chemicals which should be handled with much care.

Additional advantages and modifications will readily occur to those skilled in the art. Therefore, the invention in its broader aspects is not limited to the specific details and illustrated examples shown and described herein. Accordingly, various modifications may be made without departing from the spirit or scope of the general inventive concept as defined by the appended claims and their equivalents.

What is claimed is:

1. A method of manufacturing 2',3'-dideoxy-2'3'-didehydronucleosides represented by the following formula (I):

wherein R[1] is a silyl protective group, and B is a purine base or a pyrimidine base,
    comprising the steps of:

reacting a ribonucleoside derivative with an acid anhydride in the presence of a catalyst, said ribonucleoside derivative being of the following formula (II):

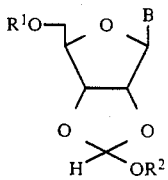

wherein $R^1$ is a silyl protective group, $R^2$ is an alkyl or phenyl group, and B is a purine or pyrimidine base, and wherein said catalyst is a member selected from the group consisting of hydrous zirconium oxide, hydrous titanium oxide, alumina, and acetic acid, and causing the resultant material to decarboxylate.

2. The method of claim 1, wherein said catalyst is hydrous zirconium oxide.

3. The method of claim 1, wherein the reaction is carried out at a temperature of from 0° to 200° C.

4. The method of claim 1, wherein the reaction is carried out for a period of from 30 minutes to 24 hours.

5. The method of claim 1, wherein said silyl protective group $R^1$ is a triorganosilyl group.

6. The method of claim 5, wherein said triorganosilyl group is a member selected from the group consisting of a trimethylsilyl group, a triethylsilyl group, a t-butyl dimethyl silyl group, and a t-butyl diphenyl silyl group.

7. The method of claim 1, wherein said silyl protective group $R^1$ contains a phenyl group.

8. The method of claim 7, wherein said phenyl group is a substituted phenyl group.

9. The method of claim 8, wherein said substituted phenyl group is substituted with a member selected from the group consisting of a halogen atom, an alkyl group, a nitro group, and an alkoxy group.

10. The method of claim 1, wherein said alkyl group $R^2$ is a member selected from the group consisting of a methyl group, an ethyl group, and a phenyl group.

11. The method of claim 10, wherein said phenyl group is a substituted phenyl group.

12. The method of claim 1, wherein said purine base B is a member selected from the group consisting of adenine, quanine, hypoxanthine, xanthine, 2-chloropurine, 6-chloropurine, 2,6-dichloropurine, 2-amino-6-chloropurine, 2,6-diaminopurine, 6-mercaptopurine, 6-methyl thiopurine, and 2-aminopurine.

13. The method of claim 1, wherein said pyrimidine base B is a member selected from the group consisting of uracil, cytosine, thymine, 5-fluorouracil, 5-chlorouracil, 5-bromouracil, 5-iodouracil, 5-ethyluracil, 5-trifluoromethyl uracil, and 5-carboxyl uracil.

14. The method of claim 1, wherein said acid anhydride is a member selected from the group consisting of acetic anhydride, chloroacetic anhydride, dichloroacetic anhydride, trichloroacetic anhydride, trifluoroacetic anhydride, benzoic anhydride, and propionic anhydride.

15. The method of claim 14, wherein said acid anhydride is used together with a solvent selected from the group consisting of xylene, N,N-dimethylformamide, butyl acetate, and nitrobenzene.

* * * * *